United States Patent [19]
Phillips

[11] Patent Number: 5,396,901
[45] Date of Patent: Mar. 14, 1995

[54] TRANSDERMAL DOSIMETER DEVICE

[76] Inventor: Michael Phillips, 156 Center Ave., Chatham, N.J. 07928

[21] Appl. No.: 179,908

[22] Filed: Jan. 11, 1994

[51] Int. Cl.⁶ .............................................. A61B 5/00
[52] U.S. Cl. .................................... 128/771; 128/632
[58] Field of Search .............. 128/632, 636, 637, 760, 128/771; 604/312

[56] References Cited

U.S. PATENT DOCUMENTS

| | | | |
|---|---|---|---|
| Re. 33,686 | 9/1991 | Parrish | 128/771 |
| 3,631,617 | 1/1972 | Pekko | |
| 4,595,011 | 6/1986 | Phillips | 128/760 |
| 4,706,676 | 11/1987 | Peck | 128/760 |
| 5,203,327 | 4/1993 | Schoendorfer et al. | 128/771 |

*Primary Examiner*—Max Hindenburg
*Attorney, Agent, or Firm*—Kane, Dalsimer, Sullivan, Kurucz, Levy, Eisele and Richard

[57] ABSTRACT

Transdermally active pharmaceutical delivery systems and dosimeters are constructed to include a tamper-indicating adhesive component for securing to the skin of a patient. If an attempt is made to remove the device, the patient's physician is alerted.

5 Claims, 1 Drawing Sheet

TRANSDERMAL DOSIMETER DEVICE

BACKGROUND OF THE INVENTION

1. Field of the Invention

The invention relates to a transdermal dosimeter, a device used to monitor human and animal exposure to chemical agents and drugs.

2. Brief Description of Related Art

A transdermal dosimeter, is a device used to monitor human exposure to chemical agents; it is based on the principle that many chemical agents are excreted through the skin in small quantities. The chemical agents may be: (a) exogenous—e.g., drugs of abuse, environmental pollutants, prescription drugs, herbicides, pesticides and the like; (b) endogenous—e.g., hormones, or metabolites such as glucose, creatinine, electrolytes or the like.

The advantage of a transdermal dosimeter is that it provides quantitative information about the mean integrated exposure to chemical agents over long periods (e.g. several hours or days), and provides evidence of exposure even after the agent may have been completely metabolized or excreted from the body. Representative of transdermal dosimeters are those described in U.S. Pat. Nos. 4,329,999; 4,595,011; and 4,706,676.

Frequently in the course of medical treatment, it is important for the physician to determine whether or not the patient is following a prescribed medical regimen, or is using alcohol or non-prescribed drugs. It is often the case that the patient does not disclose the relevant information accurately. Thus, there is a need for a monitoring device that could be used with convenience by the patient and which would yield accurate and precise information to the physician.

One of the problems or potential problems associated with the presently available devices described above, is the ability of the patient or other to remove the device from the skin for periods of time, without the physician's knowledge. This interruption of monitoring or pharmaceutical delivery, whether accidental or deliberate, knowingly or through lack of instruction, can result in inaccurate information or wrong assumptions being given to the physician.

The present invention constitutes an improvement over the devices described in the above prior art patents. The improved devices of the present invention function to alert a physician or other health-care personnel to incidences where the device has been removed, even temporarily, from the patient.

SUMMARY OF THE INVENTION

The invention comprises, in a device for the systemic transdermal collection of a sample from a mammal, which comprises;
   a container for holding the composition; and
   adhesive means on the container for adhering the container to the wearer's skin;
   the improvement, which comprises; a tamper-indicating label associated with the adhesive means whereby if the adhesion between the wearer's skin and the container is broken, the label will give an indication of such breakage.

DETAILED DESCRIPTION OF THE PREFERRED EMBODIMENTS OF THE INVENTION

Figure 1:
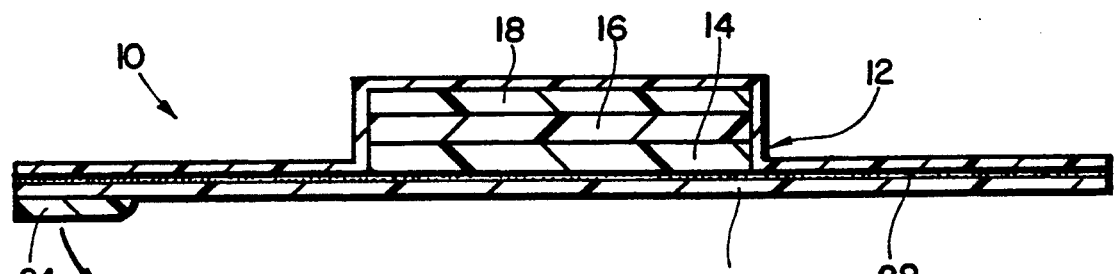
FIG. 1 is a cross-sectional side view of an embodiment transdermal dosimeter of the invention.
Figure 2:
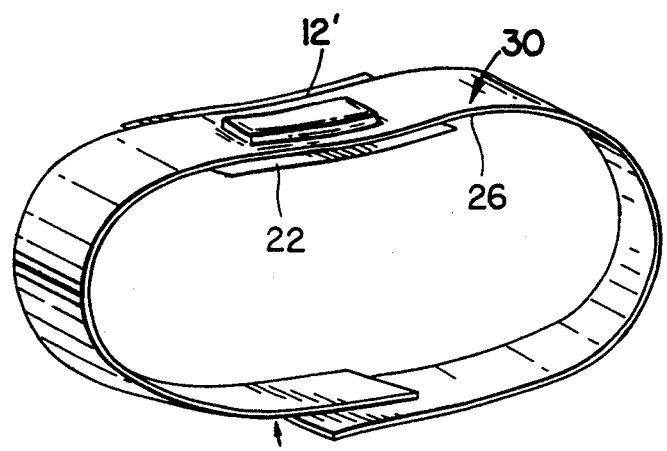
FIG. 2 is a view-in-perspective of an embodiment transdermal dosimeter of the invention prior to attachment to a patient.
Figure 3:
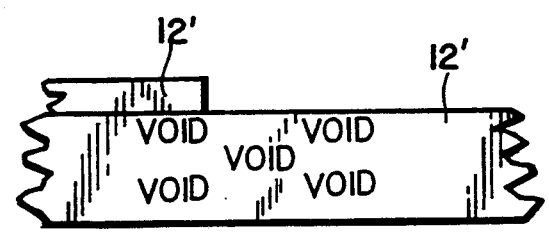
FIG. 3 is a fragmentary view of the dosimeter of FIG. 2 after removal from a patient.

Those skilled in the art will gain an appreciation of the invention from the following description of an embodiment transdermal dosimeter when read in conjunction with a viewing of the FIGS. 1-3, inclusive.

With reference to FIG. 1, a cross-sectional side elevation is seen of an improved embodiment transdermal dosimeter 10 of the invention. The transdermal dosimeter 10 is an adhesive device applied to the surface of a wearer's skin. Advantageously it is watertight, and may be worn during the normal activities of daily life, including exercise and bathing. It has four separate functions:
   (1) the facilitation of continuous transmission of substances from the surface of the skin into the device;
   (2) storage of liquid and chemical compounds;
   (3) binding of collected chemical compounds to inhibit back diffusion across the skin; or
   (4) chemical conversion of collected substances to produce an observable color change in the device.

In practice, the device is adhesively affixed to the skin of a mammal, including a human and removed several hours or days later. The chemical agent under investigation may be extracted from the dosimeter (e.g., by centrifugation if in solution or chemical elution if bound) and then assayed by conventional laboratory techniques. Alternatively, the assay may be performed in situ in the transdermal dosimeter, using such methods as enzyme-linked colorimetric reactions or head space assay of volatile compounds. The concentration of chemical substances in the device provides both qualitative and quantitative information about the intensity of the subject's exposure to the substance under investigation.

The sealed adhesive container 12 is constructed or molded from flexible pressure sensitive adhesive films or tape(s) 26. Its structure is such that it provides:
   (1) optionally a dermal contact bridge 14 for intimate contact with the surface of the skin;
   (2) watertight, chemically inert and non-allergenic character; and
   (3) aesthetics acceptable to the wearer, advantageously in the configuration of a bracelet or anklet.

The sealed adhesive container 12 may enclose three components: the dermal contact bridge 14, a collecting component 16 and a processing component 18.

The collecting component 16 contains a reservoir of immobilized isotonic fluid. The composition of the fluid phase is determined by the physico-chemical properties of the chemical compound under specific investigation. It may be:—aqueous e.g. normal or hypertonic saline (to facilitate collection of polar compounds or compounds with high water solubility)—lipid e.g. mineral oil or vegetable oil (to facilitate collection of compounds with high lipid solubility) or organic—e.g. polyethylene glycol (PEG) (to facilitate collection of compounds with intermediate solubility). The solid phase acts as a matrix to support the liquid phase. It may be cellulose based (e.g. filter paper), an inert polymer, a viscous organic compound (e.g. high molecular weight polyethylene glycol or a lipid ointment base), a semisolid material such as a gel, or any other substance capable of holding immobilized fluid in close apposition to the surface of the skin.

The second or intermediate layer 16 is the collecting component. The function of this component is to provide storage for fluid and chemical substances collected from the skin by the dermal contact bridge 14. Its composition may be:

(1) the same as the solid phase of the dermal contact bridge 14;
(2) a dry reservoir with high fluid capacity (e.g. cellulose based absorbent material or felted polyester);
(3) as a special application, either (1) or (2) impregnated with an osmotically active crystalloid material (e.g. sodium chloride, fructose, mannitol or urea) to generate an osmotic gradient across the dermal contact bridge 14 which acts as a semipermeable membrane.

The third layer is the processing component 18. The function of this component 18 is to chemically process the collected chemical substance(s) in some fashion so that they no longer remain free to diffuse back across the dermal contact bridge 14 into the skin. This serves to increase the sensitivity of the dosimeter 10. Processing occurs in either of two ways: binding or chemical conversion. When the processing component 18 acts by binding, the substance becomes physically or chemically bound. The binding agent may be a non-specific chemical binding agent (e.g., activated charcoal) or a specific binding agent (e.g., an antibody to a specific compound or drug). When the transdermal dosimeter 10 is removed from the skin, the chemical substance may be eluted from the binding agent, and assayed in the laboratory by conventional techniques. Alternatively, the processing component 18 may act by chemical conversion of the substance under investigation, to yield a colored compound and/or a more readily stored product. Examples include:—enzymic conversion of ethanol to acetaldehyde with alcohol dehydrogenase, in which the coenzyme NAD is converted to NADH, and reconversion to NAD may be accomplished by a number of dyes which change color in the process,—chemical precipitation of chloride ions with silver nitrate to form dark-colored silver chloride. This is of potential use in screening for diseases such as cystic fibrosis, in which sweat chloride excretion is impaired.

The transdermal dosimeter 10 may incorporate a number of chemical additives such as nystatin, sodium fluoride and reduced methylene blue.

The purpose of the additives is as follows:

Nystatin: Inhibits fungal proliferation. Fungi normally resident on the surface of the skin might otherwise contaminate the sweat specimen, causing (a) metabolic breakdown of ethanol (to acetaldehyde and water); and/or (b) metabolic breakdown of glucose in sweat, generating ethanol and methanol de novo.

Sodium fluoride: Inhibits anaerobic glycolysis in bacteria and fungi normally resident on skin. It provides a safeguard against any of these organisms contaminating the sweat with products of anaerobic glycolysis, e.g., ethanol.

Reduced methylene blue: In a wet patch this turns bright blue in the presence of oxygen. Hence it is a visual indicator (when the patch is removed) that the patch has leaked and/or been tampered with.

The layers 14, 16, 18 thus formed are then subjected to other necessary treatments. Thus, the dermal contact bridge 14 must be wetted with the appropriate fluid as described above. Likewise the collecting and the processing components 16, 18 may be treated with appropriate materials.

It will be appreciated by those skilled in the art that a number of structural modifications can be made to the dosimeter 10 without adversely affecting function.

For example, two modifications of the transdermal dosimeter have been successfully designed. In modification A, a transdermal dosimeter 10 is made exactly as described above, except that the dermal contact bridge 14 and the collecting component 16 are combined into a single layer i.e., the sealed adhesive container 12 covers a two-layered component rather than a three-layered component.

This may be achieved in several ways, provided that this new combined layer fulfills the functions of the two original layers i.e. (a) providing a fluid bridge in intimate contact with the surface of the skin, and (b) providing a structure that will retain body fluids as well as their dissolved chemical substances.

Structural approaches include:

(i) solid absorptive matrix (e.g. paper, cellulose fiber, polyester fiber) presoaked in fluid. The matrix can be impregnated with crystalloid or other materials, to generate an osmotic gradient across the skin; The fluid phase may be aqueous, lipid, or organic;

(ii) semi-solid absorptive matrix (e.g. a gel) capable of absorbing fluids and dissolved substances, while simultaneously functioning as a dermal contact bridge 14 in intimate contact with the surface of the skin.

In modification B, the transdermal dosimeter 10 is made exactly as described above, except that all three components under the sealed adhesive container 12 are combined into a single layer which combines their separate functions.

This may be achieved by modifying the combined dermal contact bridge 14 and collecting component 16 (described above in structural modification A) to also include the functions of the processing component 18.

There are two broad approaches to this modification:

(a) incorporation of a binding material (e.g. activated charcoal, or a resin capable of binding organic substances, such as Tenax GC) into the combined layer described in modification A;

(b) incorporation of the chemical conversion agents (described above) into the combined layer described in modification A.

The layer or layers performing the combined functions of components 14, 16, 18 are referred to herein at times as the "functional pad". A removable backing strip member 22 seals the functional pad from the atmosphere prior to affixation to the subject's skin. A longitudinally folded strip of vinyl film 24 is placed at one edge of backing member 22 by traction in the direction shown in FIG. 1 by an arrow. The vinyl film 24 acts as a grip means in facilitating the removal of the backing member 22. Further details and the method of manufacturing dosimeter 10 may be found in the U.S. Pat. No. 4,595,011 which is incorporated herein by reference thereto.

In a routine application, the backing member 22 is stripped or peeled off, thus exposing an adhesive surface 28 of the adhesive tape 26 forming sealed container 12. The unit can them be adhesively applied to the skin.

The transdermal dosimeter 10 offers many advantages. It is inexpensive to make and can be made from readily available materials such as laminate layers of synthetic polymeric resins. The device is convenient to apply and is well tolerated by wearers. It provides a simple, non-invasive method for monitoring exposure to chemical agents such as environmental toxins, prescription drugs, drugs of abuse and substances normally present in the blood which may be elevated in disease states (e.g., glucose in diabetics).

In the improved transdermal dosimeter 10 of the present invention, the sealed adhesive container 12 is constructed of chemically inert, flexible, adhesive tape 26 material impermeable to fluids and serves to contain the functional pad of the dosimeter 10. In addition, this adhesive tape 26 functions as a tamper-indicating label and wrist band which will give an indication if the transdermal dosimeter 10 is removed from the patient's skin (interrupting contact between the dermal bridge component 14 and the skin). This function is achieved by use of an adhesive tape 26 prepared by lamination of multiple layers including a support layer, a masking layer and an adhesive layer (preferably a pressure-sensitive adhesive). The support layer can bear indicia, which if uncovered from the masking layer, reveals itself as an indication of tampering. These adhesive tape 26 materials are commonly referred to and used as "tamper-proof" or security labels in the packaging industry. Representative of such materials are the laminate adhesive labels described in U.S. Pat. Nos. 3,631,617; 4,121,003; 5,042,842; and 5,153,042; all of which are hereby incorporated herein by reference thereto. A commercially available adhesive tape material preferred for use in the present invention is Scotchmark TM Label Stocks 7380, 7385 and 7385PB tamper-indicating label stocks. These laminate tapes manufactured by 3M Company (Minnesota Mining and Manufacturing Company, St. Paul, Minn.) provide a "VOID" message in the facestock when removal is attempted. Any indicia can be employed to show tampering.

FIG. 2 is a view of a preferred embodiment transdermal dosimeter 30 of the invention, wherein the container 12' functions also as a bracelet or anklet for adhering the dosimeter 30 around an ankle or wrist. Part of the adhesive tape 26 making up the container 12' has an extended or elongate portion to function as a wrist or ankle band and can overwrap or overlie portions of itself to encircle the patient's limb and adheres to itself. If removal is attempted, the indicia "Void" as shown in FIG. 3, appears to alert the physician or health care personnel to the interruption of contact between the patient's skin and the dermal contact bridge 14, i.e.; it shows that the connection forming the bracelet or anklet has been broken.

EXAMPLE

A labelstock was made using as a facestock a transparent film of biaxially oriented polyethylene terephthalate (Mylar-D TM film from E. I. DuPont de Nemours & Company, Wilmington, Del.) which is 2 mil (50 microns) thick and 50 inches (127 centimeters) wide. Onto one of the surfaces of the facestock was flexigraphically printed a release solution comprising polyvinyl alcohol dissolved in isopropyl alcohol and deionized water (Scotch TM Y-110 release solution, 3M Company, St. Paul, Minn.). The Y-110 solution has been thinned with a 75/25 parts by volume water/isopropyl alcohol solution to a #2 Zahn-cup viscosity of between 20–25 seconds at 32° C. The release coating after drying was about 200 nm in thickness and produced a repeating pattern of the word "VOID" as an indicia about 0.5 cm in height. The release-coated facestock surface was then flood coated with a transparent primer varnish of Vitel PE-200 ® polyester (E. I. DuPont de Nemours & Company, Wilmington, Del.) dissolved in ethyl acetate, n-propyl acetate, perchloroethylene and propylene glycol monomethyl ether acetate (Scotch TM Y-120 primer solution, 3M Company, St. Paul, Minn.).

Printing and coating was performed on a six color, central impression cylinder press made by Paper Converting Machine Company. Green Bay, Wis., containing six printing stations. Between each printing station were jet dryers. An additional 20 feet (6.1 m) of oven-controlled drying was present after the last of the printing stations. The release solution was applied to the web at the first station. Two print stations later the primer was applied. All dryers on the press were set at 275° (128° C.). The line was run at 300 feet (91 m) per minute. After drying, the coated facestock was rolled up into jumbo form for use in vapor coating. The dried primer formed a relatively planar surface across the coated surface of the facestock and release coating. It was 900 nm thick relative to the facestock and about 700 nm thick where it covered the release coating.

The jumbo was placed into the non-heated chamber of a vapor coater containing a heated chamber and a non-heated chamber. Aluminum bars were placed in the heated chamber and heated to 2300° F. (1200° C.). This chamber was pumped down to a pressure below 0.0005 torr and aluminum vapor was created. The facestock was then passed between nip rolls and through the heated chamber, and aluminum was condensed on the coated surface of the facestock. The line speed was about 200 feet (61 m) per minute. Aluminum was coated over the entire primed surface and formed a relatively planar surface. The aluminum layer was between 10 and 25 nm in thickness and was measured in terms of electrical resistance which was converted to light transmission at between 0.13 and 0.5 percent.

The vapor-coated aluminum surface was then laminated with an acrylic pressure-sensitive adhesive layer. The pressure-sensitive adhesive was a 94.5/5.5 percent isoctylacrylate/acrylic acid adhesive as described in Ulrich U.S. Pat. No. Re: 24,906 and U.S. Pat. No. 2,973,286 which was tackified with 65 parts Foral-85, tackifying resin in flake form (Hercules, Inc., Wilmington, Del.). The adhesive had been previously bonded to a 50 lb. (22.7 Kg), bleached densified Kraft paper with a silicone release surface on the side which was attached to the adhesive. The adhesive layer had a thickness of about 25 microns. This labelstock containing a liner was then wound up. The word "VOID" was not apparent to the observer of the surface of the labelstock.

The labelstock prepared as described above comprises:
a) a transparent facestock,
b) a transparent release coating attached to a portion of one surface of the facestock for providing an indicia,
c) a transparent primer attached to said surface of the facestock and said release coating forming a relatively continuous planar surface on said surface of the facestock,
d) a relatively planar frangible, visible, metal layer attached to said primer layer, and
e) an adhesive layer attached to said metal layer; wherein said indicia is not visible until becoming permanently visible when said facestock is separated from said release coating.

The labelstock described above is used in the present invention as the adhesive tape 26 component of the diameter 10.

I claim:

1. In a device for the transdermal collection of a composition from the physiologic system of a mammal, which comprises;

a container for holding the composition; and adhesive means on the container for adhering the container to a wearer's skin;

the improvement, which comprises; a tamper-indicating label associated with the adhesive means, said label comprising;

a) a transparent facestock, b) a transparent release coating attached to a portion of one surface of the facestock for providing an indicia, c) a transparent primer attached to said surface of the facestock and said release coating forming a relatively continuous planar surface on said surface of the facestock, d) a relatively planar frangible, visible metal layer attached to said primer layer, and e) an adhesive layer attached to said metal layer; wherein said indicia is not visible until becoming permanently visible when said facestock is separated from said release coating;

whereby if the adhesion between the skin and the container is broken, the label will give permanent indication of the breakage.

2. The improvement of claim 1 wherein the adhesive means is a multiple layer laminate of synthetic polymeric resin films.

3. The improvement of claim 1 wherein the contained composition comprises;

(a) a dermal contact bridge in the container which comprises a fluid component and a support means component for supporting the fluid component within the container;

(b) a collecting component means in the container and in contact with the dermal contact bridge, for providing storage for fluid substances collected from the dermal contact bridge; and (c) a process component in the container made of fluid absorbent material containing a chemical reagent which reacts with the stored substances, said process component being in contact with the collecting component;

said container being a partially sealed container constructed of chemically inert, flexible, fluid-tight, adhesive film material.

4. The device of claim 1 wherein the adhesive means on the container comprises a bracelet for adhesion to the mammal.

5. The device of claim 4 wherein the mammal is a human.

* * * * *